United States Patent
Childress et al.

(10) Patent No.: US 12,246,103 B2
(45) Date of Patent: Mar. 11, 2025

(54) ULTRAVIOLET LIGHT SANITIZING SYSTEM AND METHOD WITH DISTRIBUTED POWER

(71) Applicant: THE BOEING COMPANY, Chicago, IL (US)

(72) Inventors: Jamie J. Childress, Mercer Island, WA (US); Arthur Edward Brockschmidt, Jr., Renton, WA (US)

(73) Assignee: THE BOEING COMPANY, Chicago, IL (US)

(*) Notice: Subject to any disclaimer, the term of this patent is extended or adjusted under 35 U.S.C. 154(b) by 692 days.

(21) Appl. No.: 17/455,093

(22) Filed: Nov. 16, 2021

(65) Prior Publication Data
US 2022/0184252 A1 Jun. 16, 2022

Related U.S. Application Data

(60) Provisional application No. 63/124,363, filed on Dec. 11, 2020.

(51) Int. Cl.
*A61L 2/10* (2006.01)
*A61L 2/26* (2006.01)

(52) U.S. Cl.
CPC .................. *A61L 2/10* (2013.01); *A61L 2/26* (2013.01); *A61L 2202/11* (2013.01); *A61L 2202/14* (2013.01); *A61L 2202/25* (2013.01)

(58) Field of Classification Search
CPC ....... A61L 2/10; A61L 2202/25; B64D 11/00; B64D 11/02; B64D 11/04; H02J 7/0063
See application file for complete search history.

(56) References Cited

U.S. PATENT DOCUMENTS

| | | | |
|---|---|---|---|
| 6,656,424 B1 | 12/2003 | Deal | |
| 7,595,723 B2 | 9/2009 | Heitzmann et al. | |
| 8,581,522 B2 | 11/2013 | Inskeep | |
| 8,791,441 B1 | 7/2014 | Lichtblau | |
| 10,130,727 B1* | 11/2018 | Byrnes | A61L 2/24 |

(Continued)

FOREIGN PATENT DOCUMENTS

| | | | | |
|---|---|---|---|---|
| GB | 2346273 A | * | 8/2000 | H05B 41/2881 |
| JP | H10134973 A | * | 5/1998 | |
| WO | 2016210399 A2 | | 12/2016 | |

OTHER PUBLICATIONS

Schitz et al., "Power Supplies for Excilamps—A Review of Structures for UV Emission Control", 12th International Symposium on Science and Technology of Light Sources, Jul. 2010 (Year: 2010).*

(Continued)

*Primary Examiner* — Jennifer Wecker
*Assistant Examiner* — Brady C Pilsbury
(74) *Attorney, Agent, or Firm* — The Small Patent Law Group LLC; Philip S. Hof

(57) ABSTRACT

A sanitizing system and method include multiple ultraviolet (UV) lamps and a power supply module. The UV lamps each include one or more UV emitters configured to emit UV light. The UV lamps are positioned to emit the UV light towards one or more target components within a space. The power supply module is electrically connected to each of the UV lamps and configured to provide electrical energy to the UV lamps to power the UV emitters to sanitize the one or more target components.

17 Claims, 8 Drawing Sheets

(56) References Cited

U.S. PATENT DOCUMENTS

| | | | |
|---|---|---|---|
| 2004/0249369 A1 | 12/2004 | Muzzi et al. | |
| 2005/0088111 A1* | 4/2005 | Hung | H05B 41/2926 |
| | | | 315/224 |
| 2011/0243789 A1 | 10/2011 | Roberts | |
| 2012/0076702 A1 | 3/2012 | Dunkley et al. | |
| 2012/0240968 A1 | 9/2012 | Schumacher | |
| 2012/0305787 A1 | 12/2012 | Henson | |
| 2014/0044590 A1 | 2/2014 | Trapani | |
| 2015/0064065 A1 | 3/2015 | Kreitenberg | |
| 2018/0064833 A1 | 3/2018 | Childress et al. | |
| 2018/0144925 A1* | 5/2018 | Shinoda | H01J 65/00 |
| 2018/0369439 A1* | 12/2018 | Brockschmidt | H05B 41/28 |

OTHER PUBLICATIONS

Turnbull et al. "Power Electronics—Rectifiers, Filters, and Power Supplies", Reference Data for Engineers, Ninth Edition, 2002 (Year : 2002).*

European Search Report and Written Opinion for related European Application No. 21 20 7466 dated Apr. 8, 2022 (7 pages).

International Search Report for related PCT Application No. PCT/US2016/039506 dated May 31, 2017 (2 pages).

* cited by examiner

ULTRAVIOLET LIGHT SANITIZING SYSTEM AND METHOD WITH DISTRIBUTED POWER

CROSS-REFERENCE TO RELATED APPLICATIONS

The present application relates to and claims priority benefits from U.S. Provisional Application No. 63/124,363, filed Dec. 11, 2020, which is hereby incorporated by reference in its entirety.

FIELD OF THE DISCLOSURE

Embodiments of the present disclosure generally relate to ultraviolet (UV) light sanitizing systems, such as UV light sanitizing systems that may be used to sanitize or disinfect structures and areas within vehicles.

BACKGROUND OF THE DISCLOSURE

Systems are currently being developed to disinfect or otherwise sanitize surfaces within vehicles, for example, that use ultraviolet (UV) light. A UV light sanitizing system may include multiple UV lamps that emit UV light within a space. Typically, each of the UV lamps is separately and individually powered. For example, each UV lamp may have its own power circuitry for power conversion, modulation, and/or the like. The UV lamps may each have a power cable that plugs into an external power source, such as an electrical outlet. The power components, such as circuitry, cables, and connectors, add to the complexity and cost of the UV lamps. Due at least in part to the presence of the power components, the UV lamps also may be undesirably large. The large size and/or requirement to access an external power source may make installation of the UV lamps within a room difficult. Furthermore, it may be difficult to hide or conceal the UV lamps due to the size, and the conspicuous UV lamps may be aesthetically undesirable. Another drawback is that the UV lamps may not be able to be mounted proximate to the target components that are illuminated by the UV light. The energy of the UV light applied to a target surface drops considerably with increasing distance between the UV source and the target. When compared to mounting the UV lamps closer to the target, the increased distance would require emitting UV light for a longer duration and/or at a higher output level to achieve a comparable dose of UV light on the target. The longer duration and/or increased power consumption during a sanitizing process indicate reduced efficiency.

SUMMARY OF THE DISCLOSURE

A need exists for a system and a method for improving the efficiency of the sanitizing process using UV lamps, reducing cost, and increasing the flexibility and concealability of mounting UV lamps within a room. Further, a need exists for a system and a method for controlling the UV intensity and/or UV pattern over an area as desired to sanitize one or more target components positioned throughout a space. The desired UV intensity and/or pattern may vary across the area as desired.

With those needs in mind, certain embodiments of the present disclosure provide a sanitizing system that includes multiple ultraviolet (UV) lamps and a power supply module. The UV lamps each include one or more UV emitters configured to emit UV light. The UV lamps are positioned to emit the UV light towards one or more target components within a space. The power supply module is electrically connected to each of the UV lamps and configured to provide electrical energy to the UV lamps to power the UV emitters to sanitize the one or more target components.

Certain embodiments of the present disclosure provide a method for sanitizing. The method includes electrically connecting multiple ultraviolet (UV) lamps to a power supply module. Each of the UV lamps includes one or more UV emitters configured to emit UV light. The UV lamps are positioned to emit the UV light towards one or more target components within a space. The power supply module is configured to provide electrical energy to the UV lamps to power the UV emitters to sanitize the one or more target components.

Certain embodiments of the present disclosure provide a sanitizing system that includes multiple ultraviolet (UV) lamps and a power supply module. The UV lamps are mounted within a room of a vehicle. Each of the UV lamps includes one or more UV emitters configured to emit UV light. At least some of the UV lamps are disposed at spaced apart locations from one other within the room to emit the UV light towards different target components within the room. The power supply module is electrically connected to each of the UV lamps and to a vehicle electrical system. The power supply module is configured to receive electrical energy from the vehicle electrical system and distribute the electrical energy to the UV lamps via different electrically conductive leads to power the UV emitters to sanitize the target components.

Certain embodiments of the present disclosure provide a sanitizing system that includes multiple ultraviolet (UV) lamps and a power supply module configured to be electrically connected to each of the UV lamps. Each of the UV lamps includes one or more UV emitters configured to emit UV light towards one or more target components within a space. The power supply module is configured to provide electrical energy to the UV lamps to power the UV emitters to sanitize the one or more target components.

Certain embodiments of the present disclosure provide a system that includes a power supply module configured to be electrically connected to each of multiple ultraviolet (UV) lamps. The UV lamps are configured to emit UV light towards one or more target components within a space. The power supply module is configured to provide electrical energy to the UV lamps to power the UV lamps to sanitize the one or more target components.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the present disclosure provide a system and method for sanitizing (for example, disinfecting, decontaminating, cleaning, or the like) one or more components within a target space. Certain embodiments of the present disclosure provide systems and methods that allow for powering an array of multiple UV lamps by a single power supply. The power supply distributes electrical energy (e.g., power) among the array of UV lamps, and may adjust or modulate the electrical energy that is supplied to the UV lamps to control output levels of the UV light emitted by the UV lamps.

Figure 1:
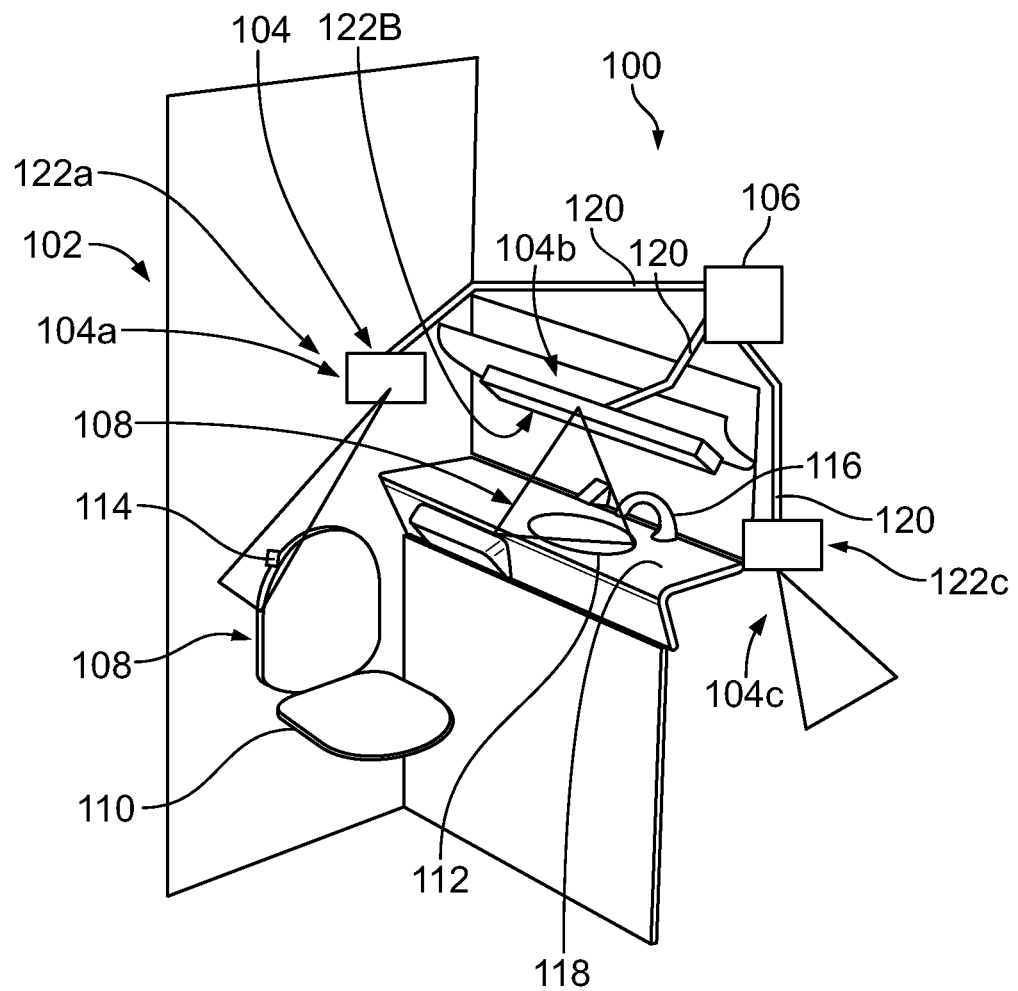
FIG. 1 illustrates a perspective view of a sanitizing system within a space, according to an embodiment of the present disclosure.

FIG. 1 illustrates a perspective view of a sanitizing system 100 within a space 102, according to an embodiment of the present disclosure. The sanitizing system 100 includes a plurality of ultraviolet (UV) lamps 104 configured to emit UV light into the space 102. In the example of FIG. 1, the plurality of UV lamps 104 includes three UV lamps. In particular, three UV lamps 104a, 104b, 104c are shown in FIG. 1. The sanitizing system 100 also includes a power supply module 106. The power supply module 106 is electrically connected to each of the UV lamps 104 and powers the UV lamps 104 to generate UV light for sanitizing (or disinfecting) the space 102. The sanitizing system 100 optionally includes more or less than three UV lamps 104 electrically connected to the power supply module 106.

In FIG. 1, the space 102 is illustrated as a lavatory. However, other spaces are possible as well. For instance, in one or more embodiments, the sanitizing system 100 may monitor and emit UV light into a space that can be any space in or around a vehicle, building, structure, facility, or the like. Further, the space may be an enclosed area or room, but need not be enclosed.

The UV lamps 104 are positioned to emit the UV light towards one or more target components 108 within the space 102 for sanitizing the target components 108 via the application of UV light. The target components 108 may have surfaces that receive frequent contact from persons that access the space 102. In the illustrated embodiment, the one or more target components 108 include a toilet 110, a sink 112, and a door of the lavatory.

Within examples, at least some of the UV lamps 104 are positioned (e.g., located and oriented) to emit UV light towards different target components 108. For example, the first UV lamp 104a is positioned to emit UV light towards the toilet 110, or at least a part of the toilet 110. The first UV lamp 104a may emit UV light towards a flush actuator 114 (e.g., lever, button, etc.) of the toilet 110. The second UV lamp 104b is positioned to emit UV light towards the sink 112 and optionally towards the surrounding region, such as a faucet 116 and/or a countertop 118. The third UV lamp 104c is positioned to emit UV light towards the door used to enter and exit the lavatory. For example, the third UV lamp 104c may be positioned to direct the UV light towards high-touch areas of the door, such as a handle, a push plate, and/or a latching mechanism for locking the door. Optionally, two or more UV lamps 104 may be positioned to emit UV light towards a common target component. Multiple UV lamps positioned to emit UV light towards a common target component can, for instance, help provide a desired total UV output to sanitize that target component, more quickly sanitize that target component, and/or reduce shadows resulting from the UV light. For example, a fourth UV lamp may be included that is also positioned to emit UV light towards the countertop 118 from a different angle relative to the second UV lamp 104b to reduce shadows.

In an example, at least some of the UV lamps 104 are mounted at spaced apart locations from one another within the space 102. For instance, the three UV lamps 104a-c in FIG. 1 are spaced apart from each other within the space 102, with UV lamp 104a at location 122a, UV lamp 104b at location 122b, and UV lamp 104c at location 122c. In an alternative embodiment, however, at least two of the UV lamps 104 may be physically adjacent and/or mechanically connected to one another. Optionally, UV lamps 104 that are located in that same or adjacent positions may still be oriented to emit UV light towards different target components 108. The spaced apart locations 122a-c of the UV lamps 104 and distance between the spaced apart locations 122a-c can be selected based on the target component or components that the UV lamp is intended to sanitize.

The power supply module 106 is electrically connected to the UV lamps 104 and provides electrical energy to power the UV lamps 104. The power supply module 106 may be an electrical device that includes processing circuitry and power modulation circuitry disposed within a case or housing. In one or more embodiments, the power supply module 106 receives electrical energy from a power source and distributes the electrical energy among the UV lamps 104. The power supply module 106 may independently control the allocation of electrical energy supplied to each of the UV lamps 104. The power supply module 106 may modify the electrical energy that is received by adjusting, converting, and/or modulating the electrical energy, and may supply the electrical energy that is modified to at least some of the UV lamps 104.

In one or more embodiments, at least some (e.g., at least one) of the UV lamps 104 are spaced-apart from the power supply module 106. For example, the power supply module 106 is discrete and spaced apart from each of the three UV lamps 104a-c in FIG. 1, and are separately mounted within the space 102. The power supply module 106 is electrically connected to the UV lamps 104 via respective electrically conductive leads 120 (also referred to herein as leads 120). Each of the leads 120 extends from the power supply module 106 to a different one of the UV lamps 104a-c to provide an electrically conductive pathway therebetween. The leads 120 may include or represent one or more insulated electrically conductive elements, such as one or more electrical wires, power cables, or the like. In another embodiment, at least one UV lamp 104 may be mechanically integrated with the power supply module 106 (instead of all UV lamps 104 spaced apart from the power supply module 106). For example, in FIG. 1, the second UV lamp 104*b* could be mechanically integrated within a housing of the power supply module 106, such that the lead 120 between the UV lamp 104*b* and the power supply module 106 is internal to the housing.

In an embodiment, the power supply module 106 and the UV lamps 104 are mounted within the space 102. For example, the UV lamps 104 may be installed on walls, a floor, or a ceiling; along the underside of structures (e.g., mirrors); on visible-light emitting light sources; and/or the like. The power supply module 106 may be installed on a wall, the ceiling, the floor, behind a structure (e.g., a mirror, vanity, etc.), or even behind a wall, above the ceiling, or below the floor. The components are fixed in place via fasteners, such as screws, clips, and/or the like. The components of the sanitizing system 100, such as the power supply module 106, the UV lamps 104, and the leads 120 may be inconspicuously installed within the lavatory to avoid interfering with the general use of the lavatory. For example, the leads 120 may be routed through or behind walls and the other components may be at least partially hidden behind walls or other structures.

The sanitizing system 100 powers multiple UV lamps from a single power supply module, which provides example benefits over known UV light systems where each UV lamp includes an individual, separate power supply, such as its own power circuitry for power conversion, modulation, and/or the like. The UV lamps may each have a power cable that plugs into an external power source, such as an electrical outlet, and/or a rechargeable battery for operational periods that do not utilize an external power source. Using the power supply module 106 to distribute electrical energy to multiple UV lamps provides several example benefits over the known UV light systems, including increased efficiency and reduced cost attributable to eliminating power circuit devices. For example, the single power supply module 106 can perform the functions of the power circuit devices integrated into the UV lamps of the known systems Eliminating the power circuit devices from the individual UV lamps permits a reduction in the size or form factor of the UV lamps, without sacrificing power output. The UV lamps 104 of the disclosed sanitizing system 100 that are each connected to the single power supply module 106 can thus be smaller than existing UV lamps that each have a different power supply module. The smaller UV lamps 104 provide improved aesthetics in the space by occupying less space. The smaller size may also enable locating the UV lamps 104 more proximate to the target components 108 within the space (relative to larger UV lamps). For example, the smaller UV lamps 104 can be inconspicuously mounted behind or within structures that would not be possible for larger UV lamps. Locating the UV lamps 104 close to target components 108 may improve energy efficiency and reduce power consumption per dosage of UV light applied to the target components 108. For example, the UV lamps 104 in FIG. 1 may be disposed within 24 inches (0.6096 meters) of the corresponding target components 108. The dose or amount of UV light applied to a surface depends on both the energy of the UV light (e.g., intensity or irradiance) and the duration of the UV light application. The energy of the UV light applied to the surface drops considerably with increasing distance between the UV source and the surface. Locating the UV lamps 104 closer to the target components 108 relative to the relative proximities of larger, conventional UV lamps, enables providing a designated UV dosage to the target components 108 by consuming less energy and/or in a shorter length of time than the same dosage applied by the larger, conventional lamps.

Another example benefit provided by the sanitizing system 100 is the ability to vary UV output as desired such that some regions within the space 102 may be illuminated with a greater irradiance or intensity of UV light than other regions within the space 102 that also receive UV light. For example, the sanitizing system 100 can modulate or adjust the operation of the UV lamps 104 individually to provide a desired UV pattern within the space 102, such as by controlling a first subset of the UV lamps 104 to emit a greater irradiance of UV light than a second subset of the UV lamps 104. The disclosed arrangement of a single power supply module 106 that power an array of small UV lamps 104 can allow regions of the illuminated field to have significantly different levels of UV. The disclosed arrangement also may provide the example benefit of increasing the available power output of the UV lamps 104 relative to existing UV lamps that are limited to a fixed power supply. For example, existing UV emitters may be limited to a specific power level, such as 12 W. The sanitizing system 100 disclosed herein may enable driving the UV lamps 104 connected to the power supply module 106 to significantly greater power levels, such as 80 W or more.

As mentioned above, in one or more embodiments, the sanitizing system 100 may monitor and emit UV light into a space 102 that can be any space in or around a vehicle, building, structure, facility, or the like. The space 102 may be an enclosed area or room, but need not be enclosed. In FIG. 1, the space 102 is a lavatory room. In embodiments in which the sanitizing system 100 is installed within vehicles, the vehicles can be passenger vehicles such as buses, trains, aircraft, marine vessels, or the like. In a commercial aircraft, the sanitizing system 100 can be located within a cargo area, a flight deck, a lavatory, a lavatory waiting area, a passenger seating area or cabin, a galley, a crew rest, an assembly area, and other areas in which individuals, passengers, flight crew, ground crew, and/or maintenance personnel may occupy or enter. For example, the space 102 of FIG. 1 may be located within a vehicle, such as within the internal cabin of a commercial aircraft. Non-limiting examples of buildings or facilities in which the sanitizing system 100 can be installed include theatres, concert venues, arenas, places of worship, banquet halls, commercial businesses, factories, hospitals, and/or the like.

The space 102 in FIG. 1 is a room that defines the space, but the sanitizing system 100 is not limited to a single room. For example, the sanitizing system 100 may be present in any space, including a space that includes multiple rooms, hallways, and the like. Using the lavatory example shown in FIG. 1, the sanitizing system 100 may optionally include one or more UV lamps disposed outside of the lavatory, such as in a galley, a passenger seating area, or the like. The power supply module 106 may distribute power to the UV lamps 104 within the lavatory and the one or more UV lamps outside of the lavatory. The sanitizing system 100 may be configured to sanitize a space defined by an internal cabin of a vehicle, or alternatively may sanitize only a portion of the internal cabin, such as only the lavatory. Optionally, a vehicle may have multiple sanitizing systems 100 disposed at different locations within the internal cabin for sanitizing different portions and target components. For example, the sanitizing system 100 shown in FIG. 1 may represent a first sanitizing system, and a second sanitizing system (the same as or similar to the sanitizing system 100) may be disposed within a passenger seating area.

Figure 2:
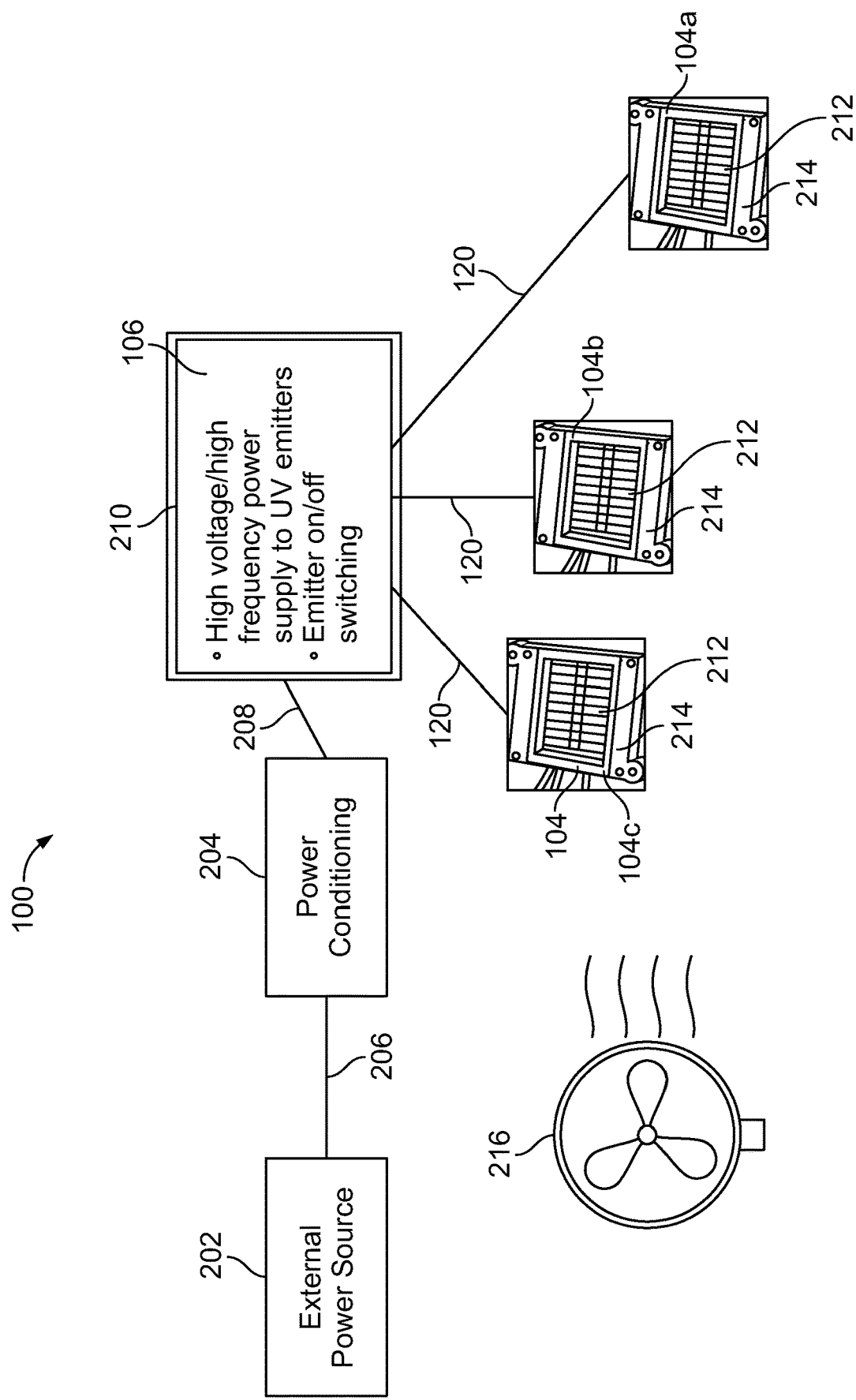
FIG. 2 illustrates a schematic diagram of the sanitizing system, according to an embodiment of the present disclosure.

FIG. 2 illustrates a schematic diagram of the sanitizing system 100 according to an embodiment of the present disclosure. In the illustrated embodiment, the power supply module 106 receives electrical energy from an external power source 202, which is separate and discrete from the power supply module 106. The power source 202 may be a vehicle electrical system onboard a vehicle or an electrical system of a building or facility. For example, the vehicle electrical system may be a power circuit that is integrated on a vehicle and powers various electrical loads, such as passenger service units (PSUs), appliances in a galley, interior lighting, air flow, and/or the like. In an alternative embodiment, the external power source 202 may be a battery, a generator, or the like.

The power supply module 106 may be electrically connected to the external power source 202 via a power conditioning circuit 204. The power conditioning circuit 204 may include one or more rectifiers, power factor correction circuits, and/or capacitors for electromagnetic interference filtering. The power conditioning circuit 204 may be electrically connected to the external power source 202 via a power cable 206. The power cable 206 may removably plug into an outlet of the vehicle electrical system, which represents the external power source 202. The power conditioning circuit 204 may be spaced apart from the power supply module 106 and electrically connected to the power supply module 106 via a power cable 208. For example, the power supply module 106 may receive electrical energy along a conductive pathway that extends from the external power source 202 along the power cable 206 to the power conditioning circuit 204, and then along the power cable 208 to the power supply module 106. In an alternative embodiment, the power conditioning circuit 204 may be integrated with the power supply module 106, such as contained within a housing 210 of the power supply module 106. The power cable 208 may be omitted in such an alternative embodiment.

In an embodiment, the power supply module 106 receives electrical energy from the power conditioning circuit 204 and controls distribution of the electrical energy among the UV lamps 104 that are connected to the power supply module 106. The electrical energy received from the power conditioning circuit 204 may be direct current (DC). For example, the power conditioning circuit 204 may receive alternating current (AC) electrical energy from the external power source 202, via the first power cable 206, and convert the AC electrical energy to DC electrical energy. The power conditioning circuit 204 may supply the DC electrical energy via the second power cable 208 to the power supply module 106. The power supply module 106 may convert the DC electrical energy to AC electrical energy, which is supplied to the UV lamps 104 via the respective electrically conductive leads 120 to power the generation of UV light.

Figure 3:
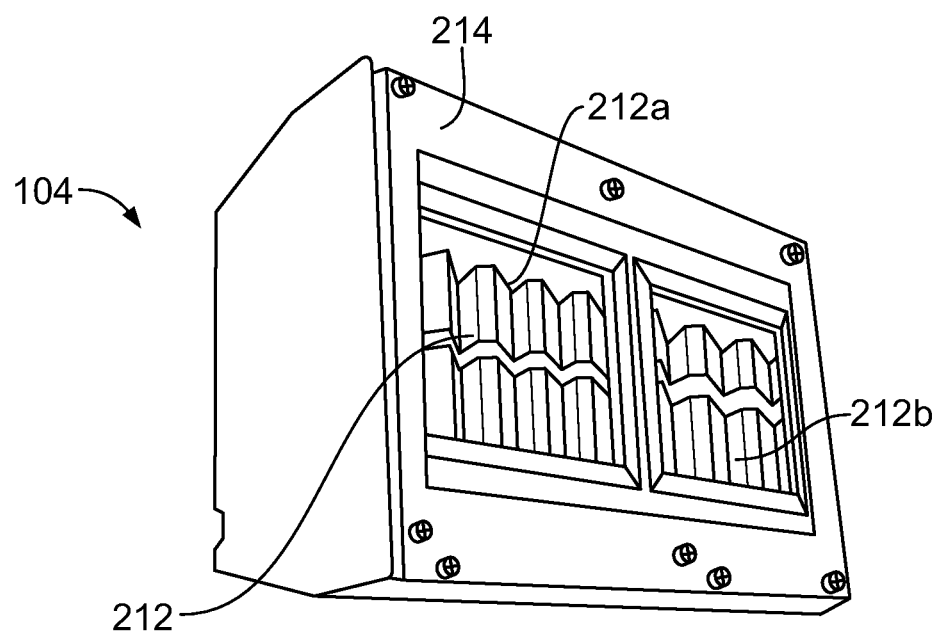
FIG. 3 illustrates an ultraviolet (UV) lamp of the sanitizing system, according to an embodiment of the present disclosure

Each of the UV lamps 104 has one or more UV emitters 212 that generate the UV light. In the illustrated embodiment in FIG. 2, each of the UV lamps 104 has one UV emitter 212. The UV lamps 104 in the sanitizing system 100 may have different numbers of UV emitters 212. For example, FIG. 3 illustrates a UV lamp 104 of the sanitizing system 100 according to an alternative embodiment. In FIG. 3, the UV lamp 104 has two UV emitters 212 (in particular, UV emitter 212a and UV emitter 212b). Optionally, at least some UV lamps 104 may have more than two UV emitters 212. Referring to both FIGS. 2 and 3, the UV emitters 212 are held by respective enclosures 214 or housings of the UV lamps 104. In an embodiment, at least some of the UV emitters 212 are excimer emitters that have a gas enclosed in a tube. The gas may include or represent a noble gas, such as krypton chloride (KrCl). In an embodiment, the enclosures 214 may be open (e.g., having a large opening) to permit airflow across the UV emitters 212 for heat dissipation. Furthermore, the openings in the enclosures 214 may be beneficial for allowing free air movement over electrodes of the UV emitters 212. If the enclosures 214 were closed, the UV may ionize air that is bounded within the enclosed area, which may require lowering an upper voltage limit of the UV lamp 104 (relative to the open enclosures) to prohibit the ionized air from arcing over.

The UV emitters 212 may operate by receiving high voltage, high frequency electrical energy, which excites the gas. The gas releases excitation energy in the form of UV photons. The UV emitters 212 may be configured to emit UV light having a wavelength within a range between 200 nm and 280 nm. For example, the UV emitters 212 may emit UV light at a narrow wavelength range centered about a designated wavelength, such as 222 nm. In a non-limiting example, the UV emitters 212 may be an excimer emitter, such as a KrCl excimer emitter. Optionally, some of the UV lamps 104 may have different types of UV emitters relative to one another. Various types of UV emitters 212 and UV lamps 104 may be utilized in the sanitizing system 100.

The UV lamps 104 may require electrical energy having relatively high voltage and relatively high frequency to provide sufficient excitation of the gases in the UV emitters 212. With reference to FIG. 2, the power supply module 106 is a high voltage and high frequency power supply. The power supply module 106 modifies the received electrical energy to provide the high voltage, high frequency electrical energy to the UV lamps 104, which is suitable and/or required to excite the gas molecules in each of the UV lamps 104. The frequency of the electrical energy supplied to the UV lamps 104 may be at least 20 kHz and no greater than 200 kHz, such as at least 50 kHz and no greater than 150 kHz. The voltage that is supplied to the UV lamps 104 from the power supply module 106 may be at least 1 kV and no greater than 10 kV, such as at least 3 kV and no greater than 5 kV.

The leads 120 extend from the housing 210 of the power supply module 106 across an intervening space to the enclosures 214 of the UV lamps 104. The high voltage and high frequency electrical energy is supplied from the power supply module 106 along the corresponding leads 120. Optionally, the UV lamps 104 may be rated to receive no more than 120 watts (W) of power, such as 80 W. The power supply module 106 includes various power modulating circuitry 304 (shown in FIG. 4) for modifying the received electrical energy to output electrical energy that has properties or characteristics that are within appropriate ranges for the UV lamps 104. The modified electrical energy may have different properties or characteristics than the received electrical energy. The power supply module 106 may also control the operations of the UV lamps 104, such as activating and deactivating the UV lamps 104, selectively activating or deactivating individual UV lamps 104, and modulating the power output of the UV lamps 104.

Optionally, the sanitizing system 100 may include one or more cooling fans 216 to actively cool the UV emitters 212. Cooling the UV emitters 212 via the cooling fan(s) 216 or another cooling mechanism may enable the UV lamps 104 to handle an increased amount of electrical energy (e.g., power level) supplied by the power supply module 106. In FIG. 2, a cooling fan 216 blows air across the UV lamps 104. Optionally, discrete cooling fans 216 could be integrated onto the enclosures 214 of the UV lamps 104 for individual cooling. The facing edges of the high voltage electrodes may be insulated as well to withstand the greater power levels.

Figure 4:
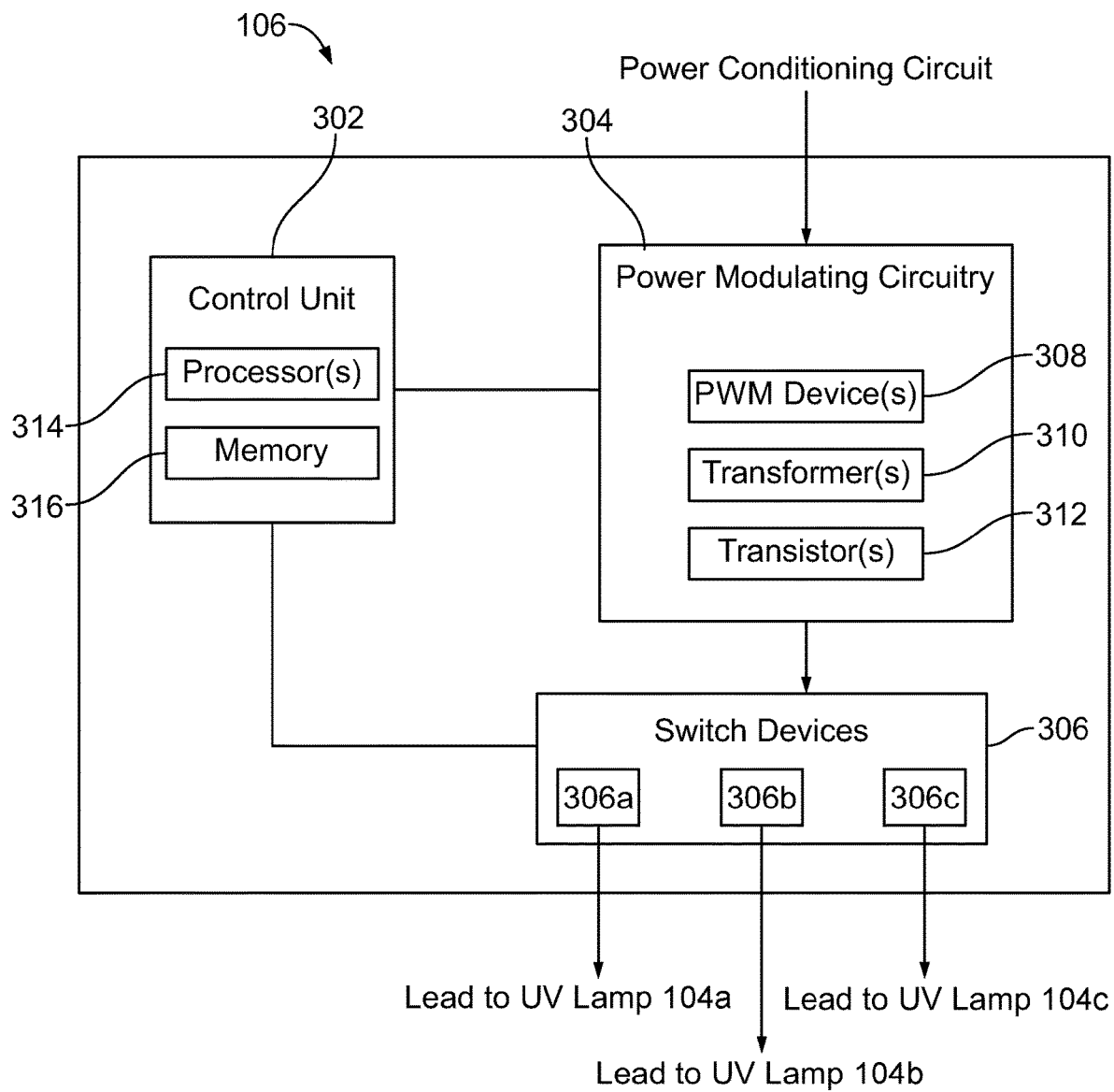
FIG. 4 illustrates a schematic block diagram of a power supply module of the sanitizing system, according to an embodiment of the present disclosure.

FIG. 4 illustrates a schematic block diagram of the power supply module 106 of the sanitizing system 100 according to an embodiment of the present disclosure. The power supply module 106 in FIG. 4 includes a control unit 302, power modulating circuitry 304, and switch devices 306. The power modulating circuitry 304 receives the electrical energy (e.g., power) from the power conditioning circuit 204. The power modulating circuitry 304 may include one or more pulse width modulation (PWM) devices 308 (e.g., pulse width modulated integrated circuits), one or more transformers 310, one or more transistors 312, and/or the like, in addition to associated circuitry such as conductive traces, resistors, and the like. The power modulating circuitry 304 and/or the power supply module 106 may include an integrated DC power supply to power the PWM devices 308. The one or more transformers 310 may be or include full bridge transformers, push-pull transformers, or the like. The one or more transistors 312 drive the transformers 310.

The switch devices 306 are electrically connected between the power modulating circuitry 304 and the leads 120 that extend to the UV lamps 104. The switch devices 306 function as gatekeepers to individually control which UV lamps 104 receive the electrical energy. For example, each switch device 306 may be associated with a different one of the leads 120 and UV lamps 104. In such an example, each of the UV lamps 104 is individually electrically connected to the power supply module 106 via a respective switch device. In the illustration shown in FIG. 2, the power supply module 106 may include three switch devices 306a, 306b, 306c to control the power supplied to each of the three UV lamps 104a-c. For example, switch device 306a controls the power supplied to the UV lamp 104a; switch device 306b controls the power supplied to UV lamp 104b; and switch device 306c controls the power supplied to UV lamp 104c. The switch devices 306 can selectively operate in an open, non-conducting state and a closed, conducting state. When the switch device 306 is in the closed state, an electrically conductive pathway is established between the power supply module 106 and a corresponding UV lamp 104 to supply power to that UV lamp 104. When the switch device 306 is in the open state, the electrically conductive pathway is blocked, which prevents the supply of power to that UV lamp 104. The switch devices 306 may be configured to withstand high voltages and high frequency current. For example, the switch devices 306 may include vacuum switches. The vacuum switches may use relays or back-to-back semiconductors, such as field effect transistors (FETs) or insulated-gate bipolar transistor (IGBTs). Conventional switch devices, like relays, may not be appropriate for use as the switch devices 306 because the high voltage, high frequency current may arc over when the relay attempts to open. In another example, the switch devices 306 may include semiconductors, such as FETs and/or IGBTs, without an associated vacuum switch. The switch devices 306 could include, for example, a pair of high voltage IGBTs arranged back-to-back or a pair of high voltage FETs arranged back-to-back.

The control unit 302 represents hardware circuitry that includes and/or is connected with one or more processors 314 (e.g., one or more microprocessors, integrated circuits, microcontrollers, field programmable gate arrays, etc.). The control unit 302 includes and/or is connected with a tangible and non-transitory computer-readable storage medium (e.g., memory) 316. For example, the memory 316 may store programmed instructions (e.g., software) that is executed by the one or more processors 314 to perform the operations of the control unit 302 described herein. The control unit 302 may be communicatively connected to the switch devices 306 and the power modulating circuitry 304 to selectively control and modulate the power supplied to the UV lamps 104. For example, the control unit 302 may send control signals to actuate the switch devices 306 between the closed and open states.

In an embodiment, each UV lamp 104 may have a switch that is communicatively connected to the switch device 306 that is associated with that specific UV lamp 104. For example, actuation of the switch on the UV lamp 104 may trigger the switch device 306 to break the conductive path and deactivate the UV lamp 104. Optionally, the UV lamps 104 may have a small auxiliary LED that is used to initiate the lamp ionization. For example, the LED may flash when power is initially received by the UV lamp 104, and the photons emitted by the LED may excite the gas within the UV emitters 212. An electrical control signal generated by the control unit 302 to actuate the switch 306 may also power the LED to initiate the lamp ionization.

The control unit 302 can control the components of the power supply module 106 to selectively distribute electrical energy with controlled power characteristics to the various UV lamps 104 in the array of UV lamps 104 to adjust UV irradiance or intensity over time and/or area within the space. For example, the control unit 302 may have multiple ways to control the output of the UV lamps 104. First, the control unit 302 can universally activate and deactivate the UV lamps 104 by selectively turning ON and OFF the UV lamps 104. For example, the control unit 302 may open each of the switch devices 306 to turn OFF the UV lamps 104, or may actuate a different, universal switch upstream of the switch devices 306 to block power to the switch devices 306.

The control unit 302 may also control the UV light output level into the space 102 by varying which UV lamps 104 are active and emitting UV light over time. By selectively actuating the switch devices 306, the control unit 302 can modify a number of the UV lamps that receive the electrical energy from the power supply module 106 during a given time period. For example, the control unit 302 may block the electrical energy to some UV lamps 104, which may as a result increase the magnitude of electrical energy (e.g., the power) delivered to other UV lamps 104 that remain active. The UV lamps 104 that are selected to the active subset may be based on various considerations, such as priority of the target components sanitized by the UV lamps, detected occupancy of a person in the area targeted by the UV lamps, and the like. For example, lower priority target components, such as components that are used and/or touched less often, may be sanitized less often than higher priority target components in the space. Furthermore, if a person is detected in a first area of the space, then the UV lamps 104 that direct UV light into the first area may be temporarily deactivated while the UV lamps 104 that direct UV light into a second area which is unoccupied may remain activated. The control unit 302 can selectively activate and deactivate the individual UV lamps 104, relative to each other, via the switch devices 306.

Another way that the control unit 302 may control the UV output of the UV lamps 104 is by modulating the electrical energy that is supplied to the UV lamps 104 via controlling the power modulating circuitry 304. For example, the control unit 302 may generate control signals to modify the transistors 312 associated with the transformers 310 and/or the PWM devices 308. Such modification may modify certain properties of the electrical energy, such as the voltage, frequency, and pulse width. In an example, the power supply module 106 (via the control unit 302) may power the UV lamps 104 at a high power level during a startup time period while the UV lamps 104 warm up. The startup time period may last about 1 second, about 0.5 seconds, or the like. After the startup time period, the power supply module 106 may power the UV lamps 104 at a nominal power level for the remainder of the operating time. The nominal power level may be lower than the high power level. For example, the high power level may be at least 30% greater than the nominal power level, such as between 30% and 50% greater than the nominal power level. The nominal power level may be less than 100 W, such as 40 W, 50 W, 60 W, or the like. The control unit 302 may be able to uniformly modulate the power to the UV lamps 104 by modifying the power modulating circuitry 304. The control unit 302 may be configured to modulate the electrical energy via the power modulating circuitry 304 and change which UV lamps 104 receive electrical energy via the switch devices 306 during a common time period.

The output levels of the UV lamps 104 may also be modulated or controlled based on the lead lengths of the electrically conductive leads 120. Referring back to FIG. 2, the leads 120 have respective lead lengths which represent the length of the lead 120 between the power supply module 106 and the UV lamp 104. The lead length may affect the UV output level limit of the UV lamps 104. For example, the longer the lead 120, the higher the capacitance, which changes resonance along the lead 120. The lap current, or an upper limit of the lap current, can be increased due to the change in resonance. This phenomenon may be applied by selecting different lead lengths to control output levels of the UV lamps 104. For example, longer lengths of leads 120 may be selected for connecting to UV lamps 104 that are desired to provide higher-energy (e.g., brighter, greater irradiance) UV light, and shorter lengths for UV lamps 104 that are permitted to emit lower-energy UV light. In FIG. 2, the lead 120 electrically connected to the first UV lamp 104*a* is longer than the leads 120 connected to the other two UV lamps 104*b*, 104*c*. Due to the longer lead 120, the first UV lamp 104*a* may inherently emit a greater output level of UV light than the second and third UV lamps 104*b*, 104*c*, even if the power supply module 106 supplies uniform electrical energy to each of the leads 120. In an example, a greater output level may be desired for a UV lamp that is farther from its corresponding target component(s) than desired for another UV lamp that is closer to its corresponding target component(s). Therefore, in an example, the length of lead 120 is selected based on the distance between the UV lamp and its corresponding target component(s). Optionally, if uniform UV output (e.g., brightness) across the array of UV lamps 104 is desired, the electrically conductive leads 120 may be formed to have the same lead length.

Figure 5:
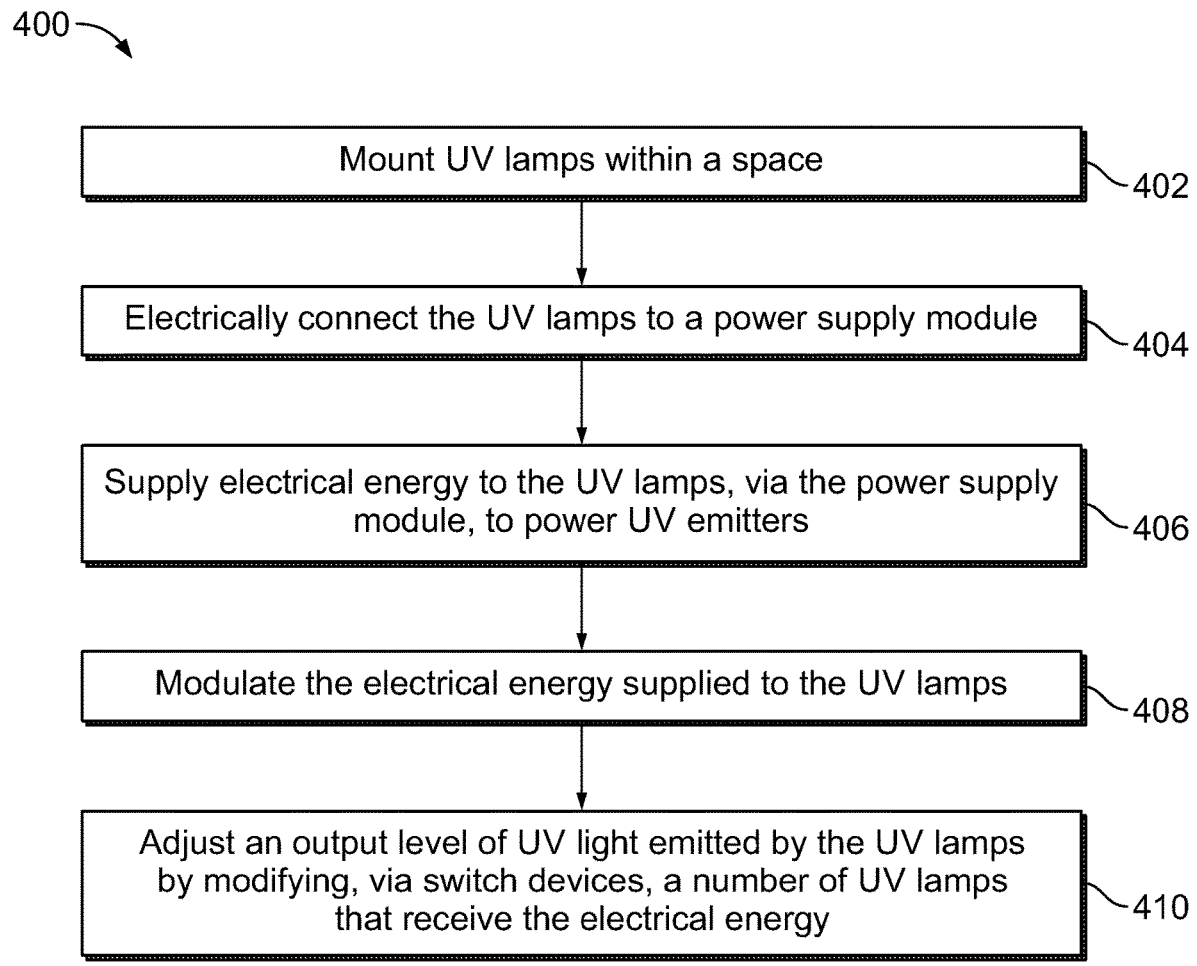
FIG. 5 illustrates a flow chart of a sanitizing method, according to an embodiment of the present disclosure.

FIG. 5 illustrates a flow chart 400 of a sanitizing method according to an embodiment of the present disclosure. Referring to FIGS. 1-5, the method begins at 402, at which UV lamps 104 are mounted within a space 102. At least some of the UV lamps 104 may be mounted at different locations within the space 102, such as proximate to different corresponding target components 108 within the space 102. At 404, the UV lamps 104 are electrically connected to a power supply module 106. The power supply module 106 may be electrically connected to the UV lamps 104 via respective electrically conductive leads 120 that extend from the UV lamps 104 to the power supply module 106.

At 406, electrical energy is supplied to the UV lamps 104, via the power supply module 106, to power UV emitters 212 of the UV lamps 104 to emit UV light into the space. At 408, the electrical energy supplied to the UV lamps 104 by the power supply module 106 is modulated. The electrical energy may be modulated based on, or due to, variations in the lead lengths of at least some of the electrically conductive leads 120 relative to one another to control UV output levels of the UV lamps 104. For example, lead length may affect the UV output power level due to inherent resonant frequencies along the length of the lead 120, so controlling the lead length ca be used to modulate the electrical energy. The electrical energy may be modulated to power the UV lamps 104 at a high power level during a startup time period, and to power the UV lamps at a nominal power level after the startup time period. The nominal power level is lower than the high power level.

At 410, the output level of the UV light emitted by the UV lamps 104 is adjusted by modifying, via switch devices 306 of the power supply module 106, a number of UV lamps 104 that receive the electrical energy from the power supply module 106.

Figure 6:
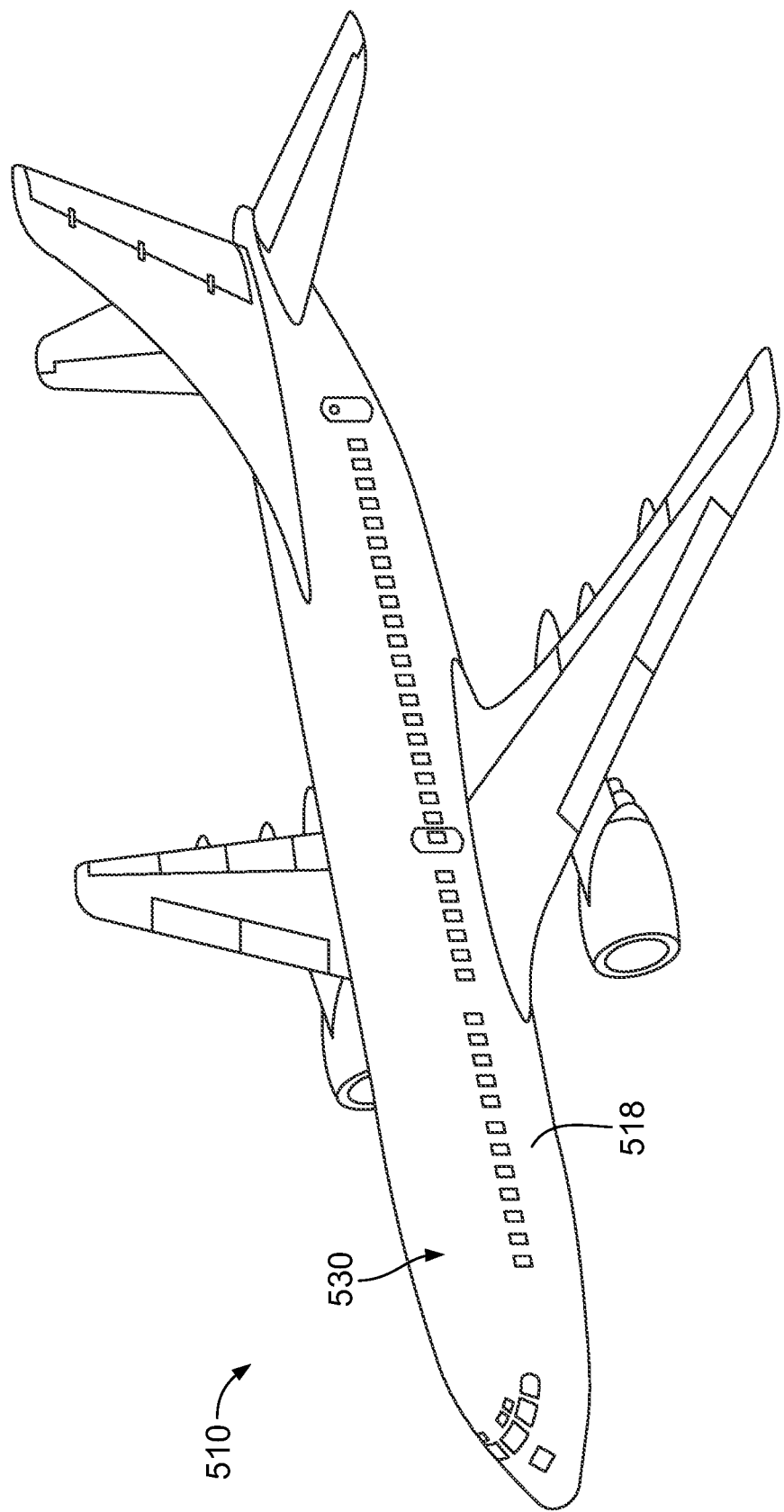
FIG. 6 illustrates a perspective top view of an aircraft, according to an embodiment of the present disclosure.

FIG. 6 illustrates a perspective top view of an aircraft 510, according to an embodiment of the present disclosure. The aircraft 510 includes a fuselage 518. While various embodiments are discussed in connection with aircraft, it may be again noted that other embodiments may be utilized in connection with, for example, other vehicle, such as ships, or ground-based vehicles such as buses or trains.

The fuselage 518 of the aircraft 510 defines an internal cabin 530, which may include a cockpit, one or more work sections (for example, galleys, personnel carry-on baggage areas, and the like), one or more passenger sections (for example, first class, business class, and coach sections), and an aft section in which an aft rest area assembly may be positioned. The internal cabin 530 includes one or more lavatories, for example, the lavatories 610 shown in FIG. 7.

Alternatively, instead of an aircraft, embodiments of the present disclosure may be used with various other vehicles, such as automobiles, buses, locomotives and train cars, watercraft, spacecraft, and the like. Further, embodiments of the present disclosure may be used with respect to fixed structures, such as commercial and residential buildings.

Figure 7:
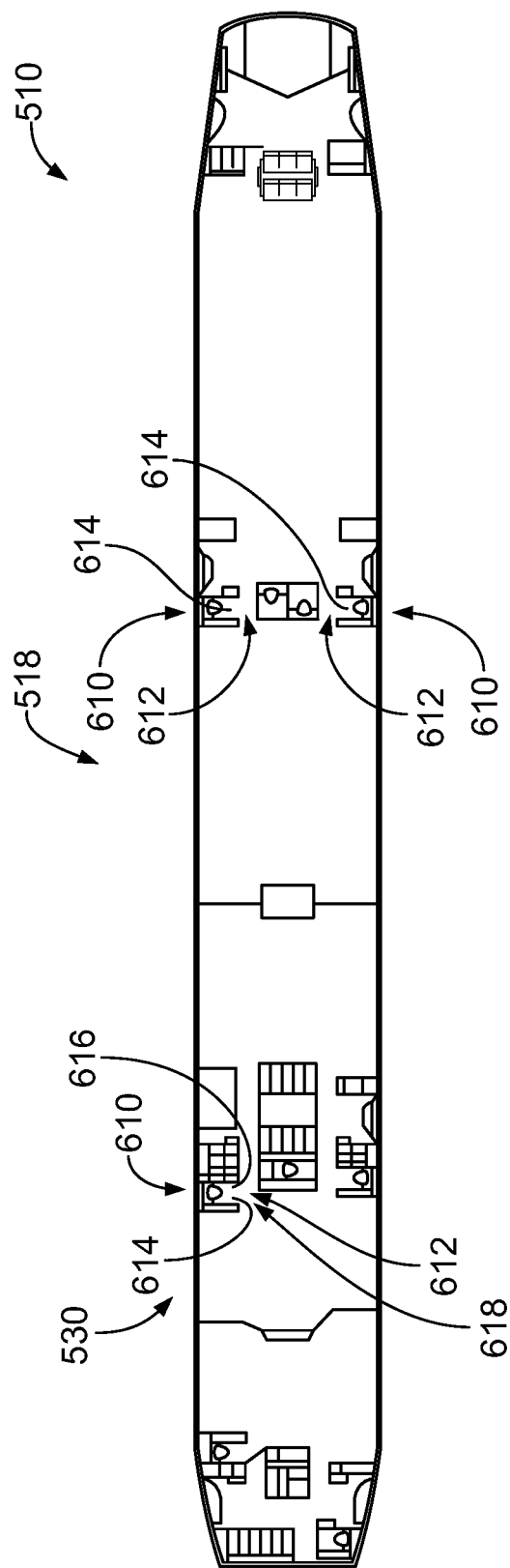
FIG. 7 illustrates a top plan view of an internal cabin of the aircraft, according to an embodiment of the present disclosure.

FIG. 7 illustrates a top plan view of the internal cabin 530 of the aircraft 510, according to an embodiment of the present disclosure. One or more lavatories 610 may be located within the internal cabin 530. Each lavatory 610 includes a lavatory floor 612. The lavatories 610 may include floor assemblies (e.g., floor assembly 614) as discussed herein, which may be secured within a portion of the fuselage. The floor assembly 614 is configured to form a portion of a floor 616 (e.g., lavatory floor 612) in an enclosed space 618 (e.g., aircraft lavatory, ship lavatory, or lavatory of ground-based vehicles such as buses or trains), or to be positioned on or in a floor 616 of an enclosed space 618.

Embodiments of the present disclosure are used to disinfect various components within a space, such as the enclosed space 618 in the internal cabin 530. Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 8:
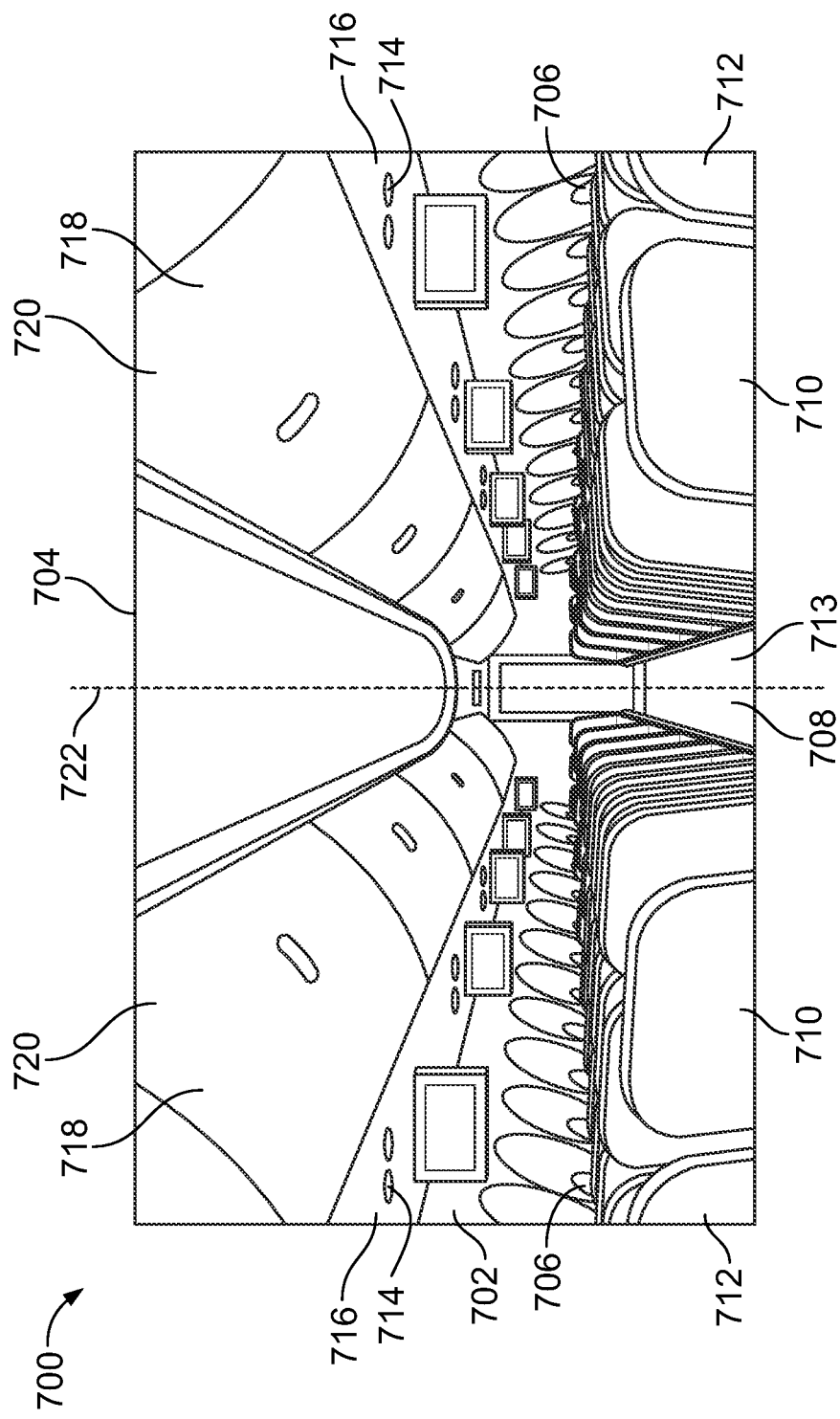
FIG. 8 illustrates a perspective interior view of an internal cabin of an aircraft, according to an embodiment of the present disclosure.

FIG. 8 illustrates a perspective interior view of an internal cabin 700 of an aircraft, according to an embodiment of the present disclosure. The internal cabin 700 includes outboard walls 702 connected to a ceiling 704. Windows 706 may be formed within the outboard walls 702. A floor 708 supports rows of seats 710. As shown in FIG. 8, a row 712 may include two seats 710 on either side of an aisle 713. However, the row 712 may include more or less seats 710 than shown. Additionally, the internal cabin 700 may include more aisles than shown.

Passenger service units (PSUs) 714 are secured between an outboard wall 702 and the ceiling 704 on either side of the aisle 713. The PSUs 714 extend between a front end and rear end of the internal cabin 700. For example, a PSU 714 may be positioned over each seat 710 within a row 712. Each PSU 714 may include a housing 716 that generally contains vents, reading lights, an oxygen bag drop panel, an attendant request button, and other such controls over each seat 710 (or groups of seats) within a row 712.

Overhead stowage bin assemblies 718 are secured to the ceiling 704 and/or the outboard wall 702 above and inboard from the PSU 714 on either side of the aisle 713. The overhead stowage bin assemblies 718 are secured over the seats 710. The overhead stowage bin assemblies 718 extend between the front and rear end of the internal cabin 700. Each stowage bin assembly 718 may include a pivot bin or bucket 720 pivotally secured to a strongback (hidden from view in FIG. 8). The overhead stowage bin assemblies 718 may be positioned above and inboard from lower surfaces of the PSUs 714. The overhead stowage bin assemblies 718 are configured to be pivoted open in order to receive passenger carry-on baggage and personal items, for example. Embodiments of the present disclosure shown and described with respect to FIGS. 1-5 may be used to sanitize various structures shown within the internal cabin 700, such as the passenger seats 710, monuments, stowage bin assemblies 718, components on and within lavatories, galley equipment and components, and/or the like.

As used herein, the term "outboard" means a position that is further away from a central longitudinal plane 722 of the internal cabin 700 as compared to another component. The term "inboard" means a position that is closer to the central longitudinal plane 722 of the internal cabin 700 as compared to another component. For example, a lower surface of a PSU 714 may be outboard in relation to a stowage bin assembly 718.

As described herein, certain embodiments of the present disclosure provide systems and methods that allow for powering an array of multiple UV lamps by a single power supply. The embodiments also provide systems and methods for using the array of UV lamps to sanitize or disinfect target components within a space, such as an internal cabin of a vehicle or an area within the internal cabin.

As used herein, the term "control unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the control unit 302 may be or include one or more processors that are configured to control operation, as described herein.

The control unit 302 is configured to execute a set of instructions that are stored in one or more data storage units or elements (such as one or more memories), in order to process data. For example, the control unit 302 may include or be coupled to one or more memories. The data storage units may also store data or other information as desired or needed. The data storage units may be in the form of an information source or a physical memory element within a processing machine.

The set of instructions may include various commands that instruct the control unit 302 as a processing machine to perform specific operations such as the methods and processes of the various embodiments of the subject matter described herein. The set of instructions may be in the form of a software program. The software may be in various forms such as system software or application software. Further, the software may be in the form of a collection of separate programs, a program subset within a larger program, or a portion of a program. The software may also include modular programming in the form of object-oriented programming. The processing of input data by the processing machine may be in response to user commands, or in response to results of previous processing, or in response to a request made by another processing machine.

The diagrams of embodiments herein may illustrate one or more control or processing units, such as the control unit 302. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the control unit 302 may represent processing circuitry such as one or more of a field programmable gate array (FPGA), application specific integrated circuit (ASIC), microprocessor(s), and/or the like. The circuits in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Further, the disclosure comprises embodiments according to the following clauses:

Clause 1. A sanitizing system comprising:
multiple ultraviolet (UV) lamps each including one or more UV emitters configured to emit UV light, wherein the UV lamps are positioned to emit the UV light towards one or more target components within a space; and
a power supply module electrically connected to each of the UV lamps and configured to provide electrical energy to the UV lamps to power the UV emitters to sanitize the one or more target components.

Clause 2. The sanitizing system of Clause 1, wherein at least some of the UV lamps are mounted at spaced apart locations from one another within the space.

Clause 3. The sanitizing system of Clause 1 or Clause 2, wherein the one or more target components include multiple target components, and at least some of the UV lamps are positioned, relative to one another, to emit the UV light towards different ones of the target components.

Clause 4. The sanitizing system of any of Clauses 1-3, wherein the power supply module is connected, via a power conditioning circuit, to an external power source.

Clause 5. The sanitizing system of Clause 4, wherein the external power source is a vehicle electrical system, and the power conditioning circuit is connected to a power cable that plugs into an outlet of the vehicle electrical system.

Clause 6. The sanitizing system of any of Clauses 1-5, wherein the power supply module is configured to receive direct current (DC) electrical energy and convert the DC electrical energy to alternating current (AC) electrical energy to power the UV lamps.

Clause 7. The sanitizing system of any of Clauses 1-6, wherein the power supply module includes one or more pulse width modulation (PWM) devices, one or more transformers, and a transistor to drive the one or more transformers.

Clause 8. The sanitizing system of any of Clauses 1-7, wherein each of the UV lamps is located within 24 inches of a corresponding target component of the one or more target components within the space.

Clause 9. The sanitizing system of any of Clauses 1-8, wherein the space is a lavatory, and at least a first UV lamp of the UV lamps is oriented to emit UV light toward a toilet of the lavatory, at least a second UV lamp of the UV lamps is oriented to emit UV light toward a sink of the lavatory, and at least a third UV lamp of the UV lamps is oriented to emit UV light toward a door of the lavatory.

Clause 10. The sanitizing system of any of Clauses 1-9, wherein the sanitizing system is positioned within a vehicle, and wherein the space is within an internal cabin of the vehicle.

Clause 11. The sanitizing system of any of Clauses 1-10, wherein each of the multiple UV lamps is connected to the power supply module via a respective electrically conductive lead, wherein at least some of the electrically conductive leads extend through the space between a housing of the power supply module and an enclosure of the respective UV lamp.

Clause 12. The sanitizing system of Clause 11, wherein at least some of the electrically conductive leads have different lead lengths relative to one another to control output levels of the UV lamps.

Clause 13. The sanitizing system of any of Clauses 1-12, wherein the power supply module is configured to power the UV lamps at a high power level during a startup time period and to power the UV lamps at a nominal power level after the startup time period, wherein the nominal power level is lower than the high power level.

Clause 14. The sanitizing system of Clause 13, wherein the nominal power level is less than 100 W supplied to each of the UV lamps.

Clause 15. The sanitizing system of any of Clauses 1-14, wherein the one or more UV emitters in at least some of the UV lamps are excimer emitters that include krypton chloride (KrCl) gas enclosed in a tube.

Clause 16. The sanitizing system of any of Clauses 1-15, wherein each of the UV lamps is individually electrically connected to the power supply module via a respective switch device comprising a vacuum switch, at least one IGBT, or at least one FET.

Clause 17. The sanitizing system of Clause 16, wherein the power supply module is configured to adjust an output level of the UV light emitted by the UV lamps by controlling the switch devices to modify a number of the UV lamps that receive the electrical energy from the power supply module.

Clause 18. The sanitizing system of any of Clauses 1-17, wherein the electrical energy that is supplied by the power supply module to power the UV lamps has a frequency at least 50 kHz and no greater than 150 kHz.

Clause 19. The sanitizing system of any of Clauses 1-18, wherein the electrical energy that is supplied by the power supply module to power the UV lamps has a voltage at least 3 kV and no greater than 5 kV Clause 20. A method for sanitizing, the method comprising:
 electrically connecting multiple ultraviolet (UV) lamps to a power supply module, each of the UV lamps including one or more UV emitters configured to emit UV light, wherein the UV lamps are positioned to emit the UV light towards one or more target components within a space, wherein the power supply module is configured to provide electrical energy to the UV lamps to power the UV emitters to sanitize the one or more target components.

Clause 21. The method of Clause 20, further comprising mounting the UV lamps within the space such that at least some of the UV lamps are mounted at spaced apart locations from one another within the space.

Clause 22. The method of Clause 20 or Clause 21, wherein electrically connecting the UV lamps to the power supply module comprises connecting each of the multiple UV lamps to the power supply module via a respective electrically conductive lead, and the method further comprises varying a lead length of at least some of the electrically conductive leads relative to one another to control output levels of the UV lamps.

Clause 23. The method of Clause 22, wherein electrically connecting the UV lamps to the power supply module further comprises connecting each electrically conductive lead to a respective switch device of the power supply module, wherein each switch device (i) comprises a vacuum switch, at least one IGBT, or at least one FET.

Clause 24. The method of any of Clauses 20-23, further comprising supplying electrical energy, via the power supply module, to the UV lamps to power the UV emitters to sanitize the one or more target components.

Clause 25. The method of Clause 24, further comprising modulating the electrical energy that is supplied to the UV lamps by the power supply module.

Clause 26. The method of any of Clauses 20-25, wherein the UV lamps are individually electrically connected to the power supply module via respective switch devices, and the method further comprises adjusting an output level of the UV light emitted by the UV lamps by controlling the switch devices to modify a number of the UV lamps that receive the electrical energy from the power supply module.

Clause 27. The method of any of Clauses 20-26, further comprising powering the UV lamps, via the power supply module, at a high power level during a startup time period, and powering the UV lamps at a nominal power level after the startup time period, wherein the nominal power level is lower than the high power level.

Clause 28. A sanitizing system comprising:
 multiple ultraviolet (UV) lamps mounted within a room of a vehicle, each of the UV lamps including one or more UV emitters configured to emit UV light, wherein at least some of the UV lamps are disposed at spaced apart locations from one other within the room to emit the UV light towards different target components within the room; and a power supply module electrically connected to each of the UV lamps and to a vehicle electrical system, wherein the power supply module is configured to receive electrical energy from the vehicle electrical system and distribute the electrical energy to the UV lamps via different electrically conductive leads to power the UV emitters to sanitize the target components.

Clause 29. The sanitizing system of Clause 28, wherein the vehicle is a commercial aircraft.

Clause 30. The sanitizing system of Clause 28 or Clause 29, wherein the room is within an internal cabin of the vehicle.

Clause 31. The sanitizing system of any of Clauses 28-30, wherein the room is a lavatory.

Clause 32. A sanitizing system comprising:
multiple ultraviolet (UV) lamps each including one or more UV emitters configured to emit UV light, wherein the UV lamps are positioned to emit the UV light towards one or more target components within a space; and
a power supply module configured to be electrically connected to each of the UV lamps, the power supply module configured to provide electrical energy to the UV lamps to power the UV emitters to sanitize the one or more target components.

Clause 33. A system comprising:
a power supply module configured to be electrically connected to each of multiple ultraviolet (UV) lamps configured to emit UV light towards one or more target components within a space, wherein the power supply module is configured to provide electrical energy to the UV lamps to power the UV lamps to sanitize the one or more target components.

Clause 34. The system of Clause 33, wherein the power supply module is configured to be electrically connected to the UV lamps via electrically conductive leads, each of the electrically conductive leads configured to extend from the power supply module to a different one of the UV lamps.

Clause 35. The system of Clause 33 or Clause 34, wherein the power supply module comprises a plurality of switch devices, wherein each switch device (i) comprises a vacuum switch, at least one IGBT, or at least one FET, and (ii) is configured to electrically connect the power supply module to a respective UV lamp of the multiple UV lamps.

Clause 36. The system of any of Clauses 33-35, wherein the power supply module further comprises a power modulating circuitry that includes one or more pulse width modulation (PWM) devices, one or more transformers, and a transistor to drive the one or more transformers.

Clause 37. The system of Clause 35 and Clause 36, wherein the power supply module further comprises a control unit, the control unit communicatively connected to the plurality of switch devices and the power modulating circuitry and configured to selectively control and modulate the power supplied to the UV lamps via the switch devices and the power modulating circuitry.

Clause 38. The system of Clause 33, further comprising a power conditioning circuit connected to the power supply module, the power conditioning circuit configured to (i) receive alternating current (AC) electrical energy from an external power source, via a first power cable, and convert the AC electrical energy to direct current (DC) electrical energy and (ii) supply the DC electrical energy via a second power cable to the power supply module.

Clause 39. The system of any of Clauses 33-38, wherein the power supply module is configured to modulate the electrical energy that is supplied to the UV lamps to adjust output levels of the UV light emitted by the UV lamps.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:
1. A sanitizing system comprising:
multiple ultraviolet (UV) lamps each including one or more UV emitters configured to emit UV light, wherein the UV lamps are positioned to emit the UV light towards target components within a space, so that a first UV lamp of the UV lamps is positioned to emit UV light towards a first target component within the space and a second UV lamp of the UV lamps is positioned to emit UV light towards a second target component within the space; and a power supply module electrically connected to each of the UV lamps and configured to provide electrical energy to the UV lamps to power the UV emitters to sanitize the target components, wherein the UV lamps are connected to the power supply module via different respective electrically conductive leads that each extend from a housing of the power supply module to an enclosure of a different corresponding UV lamp, wherein at least some of the electrically conductive leads have different lead lengths relative to one another to vary output levels of the UV light emitted by the UV lamps, wherein the different lead lengths are selected based on different distances between the UV lamps and the target components so that a first electrically conductive lead connected to the first UV lamp is longer than a second electrically conductive lead connected to the second UV lamp based on a first distance from the first UV lamp to the first target component being greater than a second distance from the second UV lamp to the second target component.

2. The sanitizing system of claim 1, wherein at least some of the UV lamps are mounted at spaced apart locations from one another within the space.

3. The sanitizing system of claim 1, wherein the power supply module is connected, via a power conditioning circuit, to an external power source.

4. The sanitizing system of claim 3, wherein the external power source is a vehicle electrical system, and the power conditioning circuit is connected to a power cable that plugs into an outlet of the vehicle electrical system.

5. The sanitizing system of claim 1, wherein the power supply module is configured to receive direct current (DC) electrical energy and convert the DC electrical energy to alternating current (AC) electrical energy to power the UV lamps.

6. The sanitizing system of claim 1, wherein the power supply module includes one or more pulse width modulation (PWM) devices, one or more transformers, and a transistor to drive the one or more transformers.

7. The sanitizing system of claim 1, wherein the space is a lavatory, and at least a first UV lamp of the UV lamps is oriented to emit UV light toward a toilet of the lavatory, at least a second UV lamp of the UV lamps is oriented to emit UV light toward a sink of the lavatory, and at least a third UV lamp of the UV lamps is oriented to emit UV light toward a door of the lavatory.

8. The sanitizing system of claim 1, wherein the power supply module is configured to power the UV lamps at a high power level during a startup time period and to power the UV lamps at a nominal power level after the startup time period, wherein the nominal power level is lower than the high power level.

9. The sanitizing system of claim 8, wherein the nominal power level is less than 100 W supplied to each of the UV lamps.

10. The sanitizing system of claim 1, wherein each of the UV lamps is individually electrically connected to the power supply module via a respective switch device comprising a vacuum switch, at least one IGBT, or at least one FET.

11. The sanitizing system of claim 10, wherein the power supply module is configured to adjust the output levels of the UV light emitted by the UV lamps by controlling the switch devices to modify a number of the UV lamps that receive the electrical energy from the power supply module.

12. The sanitizing system of claim 1, wherein the electrical energy that is supplied by the power supply module to power the UV lamps has a frequency at least 50 kHz and no greater than 150 kHz.

13. The sanitizing system of claim 1, wherein the UV lamps are positioned so that the respective distance between each UV lamp of the UV lamps and the corresponding target component of the target components to which the UV lamp is aimed is no greater than 24 inches.

14. A method for sanitizing, the method comprising:
electrically connecting multiple ultraviolet (UV) lamps to a power supply module, each of the UV lamps including one or more UV emitters configured to emit UV light, wherein the UV lamps are positioned to emit the UV light towards one or more target components within a space, wherein the power supply module is configured to provide electrical energy to the UV lamps to power the UV emitters to sanitize the one or more target components, wherein electrically connecting the UV lamps to the power supply module comprises connecting the UV lamps to the power supply module via different respective electrically conductive leads that each extend from a housing of the power supply module to an enclosure of a different corresponding UV lamp, wherein at least some of the electrically conductive leads have different lead lengths relative to one another to vary output levels of the UV light emitted by the UV lamps, wherein the different lead lengths are selected based on different distances between the UV lamps and the one or more target components within the space.

15. The method of claim 14, wherein electrically connecting the UV lamps to the power supply module further comprises connecting each electrically conductive lead to a respective switch device of the power supply module, wherein each switch device (i) comprises a vacuum switch, at least one IGBT, or at least one FET.

16. The method of claim 14, wherein the UV lamps are individually electrically connected to the power supply module via respective switch devices, and the method further comprises adjusting the output levels of the UV light emitted by the UV lamps by controlling the switch devices to modify a number of the UV lamps that receive the electrical energy from the power supply module.

17. A sanitizing system comprising:
multiple ultraviolet (UV) lamps mounted within a room of a vehicle, each of the UV lamps including one or more UV emitters configured to emit UV light, wherein at least some of the UV lamps are disposed at spaced apart locations from one other within the room to emit the UV light towards different target components within the room, so that a first UV lamp of the UV lamps is positioned to emit UV light towards a first target component within the room and a second UV lamp of the UV lamps is positioned to emit UV light towards a second target component within the room; and a power supply module electrically connected to each of the UV lamps and to a vehicle electrical system, wherein the power supply module is configured to receive electrical energy from the vehicle electrical system and distribute the electrical energy to the UV lamps via different electrically conductive leads to power the UV emitters to sanitize the target components, wherein at least some of the electrically conductive leads have different lead lengths relative to one another to vary output levels of the UV light emitted by the UV lamps, wherein the different lead lengths are selected based on different distances between the UV lamps and the corresponding target components, so that a first electrically conductive lead connected to the first UV lamp is longer than a second electrically conductive lead connected to the second UV lamp based on a first distance from the first UV lamp to the first target component being greater than a second distance from the second UV lamp to the second target component.

* * * * *